(12) United States Patent
Brégeon et al.

(10) Patent No.: US 11,599,991 B2
(45) Date of Patent: Mar. 7, 2023

(54) PROCESS FOR DIAGNOSING CHRONIC INFLAMMATORY INTESTINAL DISEASES

(71) Applicants: UNIVERSITÉ DE NANTES, Nantes (FR); CHU DE NANTES—CENTRE HOSPITALIER UNIVERSITAIRE DE NANTES, Nantes (FR); INSERM—INSTITUT NATIONAL DE LA SANTÉ ET DE LA RECHERCHE MÉDICALE, Paris (FR)

(72) Inventors: Jérémy Brégeon, Orvault (FR); Michel Neunlist, Nantes (FR); Emmanuel Coron, Nantes (FR)

(73) Assignees: UNIVERSITÉ DE NANTES, Nantes (FR); CHU DE NANTES—CENTRE HOSPITALIER UNIVERSITAIRE DE NANTES, Nantes (FR); INSERM—INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 743 days.

(21) Appl. No.: 16/085,993

(22) PCT Filed: Mar. 15, 2017

(86) PCT No.: PCT/FR2017/050586
§ 371 (c)(1),
(2) Date: Jun. 23, 2020

(87) PCT Pub. No.: WO2017/158286
PCT Pub. Date: Sep. 21, 2017

(65) Prior Publication Data
US 2020/0311910 A1   Oct. 1, 2020

(30) Foreign Application Priority Data
Mar. 15, 2016  (FR) ..................................... 1652150

(51) Int. Cl.
*G06K 9/00*          (2022.01)
*G06T 7/00*          (2017.01)
(Continued)

(52) U.S. Cl.
CPC ........... *G06T 7/0012* (2013.01); *G16H 30/40* (2018.01); *G16H 50/20* (2018.01); *G16H 70/60* (2018.01);
(Continued)

(58) Field of Classification Search
CPC ........ G16H 70/60; G16H 50/20; G16H 30/40; G06T 2207/10056; G06T 2207/10068;
(Continued)

(56) References Cited

U.S. PATENT DOCUMENTS 8,682,142 B1    3/2014  Boskovitz et al.
2018/0365831 A1*  12/2018  Popp ..................... G06T 7/0012

FOREIGN PATENT DOCUMENTS

AU    2007203559 A1    9/2007
JP    2003-510112 A    3/2003
(Continued)

OTHER PUBLICATIONS

J. Bregeon, E. Coron, A. C. C. Da Silva, J. Jaulin, P. Aubert, J. Chevalier, N. Vergnolle, G. Meurette and M. Neunlist,"Sacral nerve stimulation enhances early intestinal mucosal repair following mucosal injury in a pig model", J Physiol 594.15 first published online Mar. 4, 2016, pp. 4309-4323 (Year: 2016).*
(Continued)

*Primary Examiner* — Atiba O Fitzpatrick
(74) *Attorney, Agent, or Firm* — Kenealy Vaidya LLP (57) ABSTRACT

Some embodiments are directed to a process for quantifying changes in the intestinal mucosa caused by a chronic inflam-
(Continued)

matory intestinal disease in individuals, an ex vivo process for diagnosing a chronic inflammatory intestinal disease in individuals, and an ex vivo process for the differential diagnosis of Crohn's disease versus ulcerative colitis in individuals.

19 Claims, 7 Drawing Sheets

(51) Int. Cl.
    *G16H 70/60*      (2018.01)
    *G16H 50/20*      (2018.01)
    *G16H 30/40*      (2018.01)

(52) U.S. Cl.
    CPC .............. *G06T 2207/10056* (2013.01); *G06T 2207/10068* (2013.01); *G06T 2207/30028* (2013.01)

(58) Field of Classification Search
    CPC . G06T 2207/30028; G06T 2207/10064; G06T 7/0012–0016; G06T 2207/30004–30104; G06T 7/10–194; G06T 2207/20112; A61B 5/0068; A61B 1/31–313; A61B 1/273; A61B 5/0071; A61B 1/043; A61B 5/4255; A61B 5/7485; G01N 21/64–6458; G01N 2800/06; G01N 2800/065; A61P 1/00–04; G06V 2201/03; G06V 20/695; G06V 40/162; G06K 9/6224
    See application file for complete search history.

(56) References Cited

FOREIGN PATENT DOCUMENTS

| | | |
|---|---|---|
| JP | 2012-503475 A | 2/2012 |
| JP | 2012-73179 A | 4/2012 |

OTHER PUBLICATIONS

Leda Roncoroni1, Luca Elli, Maria Teresa Bardella, "Extracellular matrix proteins and displacement of cultured fibroblasts from duodenal biopsies in celiac patients and controls", Journal of Translational Medicine 2013, 11:91 (Year: 2013).*

Weston A. Welge, Jennifer K. Barton, "Expanding Functionality of Commercial Optical Coherence Tomography Systems by Integrating a Custom Endoscope", PLOS ONE | DOI:10.1371/journal.pone.0139396 Sep. 29, 2015, pp. 1-15 (Year: 2015).*

Buda, A., et al., "Confocal laser endomicroscopy for prediction of disease relapse in ulcerative colitis: A pilot study," J. Crohn's and Colitis 2014;8:304-311.

Macé, V., et al., "Confocal laser endomicroscopy: A new gold standard for the assessment of mucosal healing in ulcerative colitis," J. Gastroenterol. Hepatol. 2015;30 (Suppl 1):85-92.

Morpurgo, M., et al., "Detection of a fluorescent-labeled avidin-nucleic acid nanoassembly by confocal laser endomicroscopy in the microvasculature of chronically inflamed intestinal mucosa," Int. J. Nanomed. 2015;10:399-408.

Mazzuoli, S., et al., "Definition and evaluation of mucosal healing in clinical practice," Digestive and Liver Disease 2013;45:969-977.

Tontini, G. E., et al., "P167 Prediction of clinical outcome in Crohn's disease by using confocal laser endomicroscopy: a prospective, observational, follow-up study," J. Crohn's and Colitis 2014;8:S131.

Arsenescu, R., et al., "Probe-Based Confocal Laser Endomicroscopy (pCLE) Provides Reliable, Real Time Assessment During Colonoscopy in Patients With Inflammatory Bowel Disease," Gastroenterol. 2014;146(5—Suppl. 1):S219.

Taylan, K., et al., "Enteroscopic findings of Celiac Disease and their correlation with mucosal histopathologic changes," Computer in Biology and Medicine 2015;65:315-319.

Keuchel, M., et al., "Quantitative measurements in capsule endoscopy," Computers in Biology and Medicine 2015;65:333-347.

Rodriguez-Diaz, E., et al., "Elastic Scattering Spectroscopy as an Optical Marker of Inflammatory Bowel Disease Activity and Subtypes," Inflammatory Bowel Diseases 2014;20(6):1029-1036.

Gheorghe, C., et al., "Endomicroscopy for assessing mucosal healing in patients with ulcerative colitis," J. Gastrointest. Liver Dis. 2011;20(4):423-426.

Chernavskaia, O., et al., "Beyond endoscopic assessment in inflammatory bowel disease: real-time histology of diseases activity by non-linear multimodal imaging," Scientific Reports 2016;6:29239.

International Search Report and Written Opinion for PCT Patent App. No. PCT/FR2017/050586 (dated May 4, 2017) with English translation.

* cited by examiner

PROCESS FOR DIAGNOSING CHRONIC INFLAMMATORY INTESTINAL DISEASES

CROSS REFERENCE TO RELATED APPLICATIONS

This application is a national phase filing under 35 C.F.R. § 371 of and claims priority to PCT Patent Application No. PCT/FR2017/050586, filed on Mar. 15, 2017, which claims the priority benefit under 35 U.S.C. § 119 of French Patent Application No. 1652150, filed on Mar. 15, 2016, the contents of each of which are hereby incorporated in their entireties by reference.

BACKGROUND

Some embodiments relate to a process for quantifying modifications of the intestinal mucosa induced by a chronic inflammatory bowel disease in an individual, to an ex vivo process for diagnosing a chronic inflammatory bowel disease in an individual, and also to an ex vivo process for the differential diagnosis of Crohn's disease versus ulcerative colitis in an individual.

Some of these and other embodiments can be applied in the medical, in particular diagnostic, field.

In the description below, the references between square brackets ([ ]) refer to the list of references provided at the end of the text.

Crohn's disease is a chronic inflammatory disease that can affect any segment of the digestive tract, but more particularly the terminal small intestine (ileum) and the colon, and can be accompanied by extra-intestinal (joint, skin, ocular, etc.) manifestations. In France, it has an incidence of about 5 per 100,000 inhabitants per year. Even though Crohn's disease can occur at any age, it is usually diagnosed between 20 and 30 years of age. It is a cryptogenetic disease, wherein various factors are found and discussed (genetic predisposition, immunological and environmental factors). It is, moreover, promoted by smoking and lifestyle in industrialized countries.

The diagnosis of Crohn's disease is based on a cluster of arguments, both clinical and paraclinical. Diagnosis is usually established at the time of an attack. The clinical manifestations depend on the location of the disease: abdominal pain, diarrhea and/or dysenteric syndrome, which is usually mucohemorrhagic, involvement of the anoperineal region, sometimes with general signs and/or systemic manifestations. Biological abnormalities (inflammatory syndrome, deficiencies, etc.) become readily associated therewith. Thus, the diagnosis of Crohn's disease can be difficult and can require the other causes of organic intestinal harm (infectious, ischemic, drug-related, radiation-induced or even neoplastic) to be discarded. Furthermore, the distinction between Crohn's, in particular colonic disease, and ulcerative colitis can be tricky.

With ulcerative colitis, Crohn's disease (CD) is among the diseases referred to as IBD: chronic inflammatory bowel diseases. Ulcerative colitis (or "UC") is a persistent inflammation of the intestinal mucosa. It usually affects the rectum and, in a more or less widespread manner, the colon. UC is an ailment which is characterized by alternating phases of activity (or "attacks"), of variable intensity, and of symptomless phases. This ailment, which is more common in industrialized countries, is thought to be promoted by genetic predispositions and immune system dysfunction.

At the current time, there are few clinical or biological criteria for differentiating CD, in particular colonic CD (Tontini et al., World J. Gastroenterol, 2016 Jan. 21, Tontini et al., World J. Gastroenterol, 2016 Jan. 21, 2016 January 21; 22(3): 246-59 ([1])), from UC, or for predicting the progression of the disease, that is to say relapse or response to treatments.

Numerous inflammatory gastrointestinal diseases are characterized by structural changes in the mucosa. These modifications correlate with the seriousness of the disease, and can be a predictive factor for progression or for response to treatment.

Among the principal structural characteristics used for the diagnosis of colonic lesions of the mucosa, study of the profile of crypt wells (PPCs) is widely recognized. The methods for detecting PPC remain essentially descriptive, although recent studies have shown that a quantitative and computer-based image analysis approach increases the sensitivity of classification and decreases analysis variation between operators.

Among the methods used for imaging the intestinal mucosa, confocal endomicroscopy (CEM) is an innovative real-time technique. CEM is an endoscopic imaging technique which makes it possible to examine the digestive mucosa at a cell level.

SUMMARY

However, at the current time, although there are studies which have established qualitative classifications by CEM of IBDs, few studies have carried out a quantitative analysis of these modifications.

The only studies carried out have related to the analysis of the severity of the inflammation in CD or UC.

Kiesslich et al. propose a classification of the severity of the inflammation of ulcerative colitis in three grades (None, Medium to moderate, Severe). This classification is based:
1—on modifications of the architecture of the intestinal crypt, of the distribution of the crypts in the mucosa,
2—on the presence of a cell infiltrate in the mucosa,
3—on the modifications of the architecture of the mucosal blood vessels.

These criteria are evaluated qualitatively by the operator (Gastroenterology 2007, 132:874-882 ([2])).

Li et al. propose a classification of ulcerative colitis in four grades (from A to D) according to morphological criteria of the colonic crypt and arrangement of the crypts in the mucosa, assessed qualitatively by the operator (Am J Gastroenterol 2010; 105:1391-1396 ([3])). This analysis correlates significantly with the histological analysis.

Neumann et al. also demonstrate the usefulness of confocal endomicroscopy for evaluating Crohn's disease and propose a Crohn's disease endomicroscopic activity score based on an evaluation of the architectural modifications of the crypts, of the vessels and of the *Lamina propria* (Inflamm Bowel Dis. 2012 December; 18(12):2261-9 ([4])).

Liu et al. have quantified the density of "epithelial holes" in patients suffering from Crohn's disease or ulcerative colitis. They have demonstrated a significant increase in the density of these "holes" in the sick population compared with the healthy population (Gastrointest. Endosc. 2011, 73:1174-1180 ([5])).

Musquer et al. have quantified the ratio of the axes of opening of the lumen of the colonic crypts in patients suffering from Crohn's disease and have established a link between an increase in this ratio and the presence of the disease and its stage (remission/inflammation) (Dig Liver Dis 2013, 45:487-492 ([6])).

It may therefore be advantageous to provide diagnostic tools that address or overcome these defects, drawbacks and obstacles of the related art, in particular for a process which makes it possible to master the diagnosis of IBDs, and in particular to distinguish between CD and UC.

Some embodiments make it possible precisely to address, solve, and/or overcome the abovementioned obstacles and drawbacks of the related art by providing, on the one hand, a method of analysis and also characteristic parameters of IBDs, and on the other hand, the application of this method for distinguishing healthy patients from IBD patients.

Some embodiments also provide IBD imaging biomarkers.

The applicant has succeeded in developing, at the end of extensive research studies, a process based on image analysis, in particular endomicroscopic-image analysis, and has thus defined a score resulting from the quantitative analysis of these images, the data making it possible to meet the needs defined above.

The applicant has in particular developed a method for differential diagnosis based on the analysis of confocal endomicroscopy (CEM) images. The applicant surprisingly uses CEM for evaluating the structural changes of the mucosa in inflammatory bowel diseases and performing a diagnosis of IBDs, and also a differential diagnosis of CD vs. UC.

The quantitative score created by the applicant advantageously makes it possible to distinguish CD from UC with a positive predictive factor of approximately 83.3% for CD and of approximately 100% for UC. Advantageously, the CD diagnosis sensitivity is approximately 100% with a specificity of approximately 87.5%. The UC diagnosis sensitivity is advantageously approximately 81.8% with a specificity of approximately 100%.

The score proposed is based on a simple examination carried out by a gastroenterologist, without anesthesia, without biopsies or techniques requiring coproculture.

Advantageously, the score proposed allows a direct diagnosis, i.e. without time required for processing by another department.

Advantageously, the method proposed can be implemented with other imaging techniques which provide dynamic images of the microscopic architecture of the digestive mucosa, such as the images obtained by use of endocytoscopes and/or endoscopes at high magnification.

Thus, a first embodiment relates to an ex vivo process for quantifying the modifications of the intestinal mucosa possibly induced by a chronic inflammatory bowel disease in an individual, the process including:

1) measuring, on a confocal endomicroscopic image of the digestive mucosa of an individual, the following crypt well profile (PPC) parameters:
   a) Fluorescence leakage of the mucosa (FL),
   b) Perimeter of opening of the crypt well (PO),
   c) Sphericity of the crypt well (Spher),
   d) Roundness of the crypt well (Round),
   e) Feret diameter of the crypt well (Feret),
   f) Crypt well elongation factor (EF),
   g) Ratio of the axes of opening of the crypt well (Ma/ma),
   h) Crypt density per field (Dens); and
2) quantifying the modifications of the parameters a) to h) compared with the corresponding parameters of a healthy individual.

For the purposes of some embodiments, the expression "modifications of the intestinal mucosa possibly induced by a chronic inflammatory bowel disease" is intended to mean any microscopic, in particular cellular, modification of the intestinal mucosa caused by inflammation due to IBD. They may for example be modifications of the structure of the crypt wells of the colonic mucosa and/or of the cells forming the wells. The modification may be architectural and/or dynamic. For example, the modification may relate to at least one of the following parameters: fluorescence leakage of the mucosa (FL), perimeter of opening of the crypt well (PO), sphericity of the crypt well (Spher), roundness of the crypt well (Round), Feret diameter of the crypt well (Feret), crypt well elongation factor (EF), ratio of the axes of opening of the crypt well (Ma/ma), crypt density per field (Dens).

For the purposes of some embodiments, the term "digestive mucosa" is intended to mean all or part of the most superficial layer of epithelial cells of the wall of the digestive tract.

For the implementation of some embodiments, the digestive mucosa denotes all or part of the intestinal mucosa. It may, for example, be all or part of the colonic mucosa.

The process of some embodiments makes it possible, on a medical image of all or part of the digestive mucosa of an individual, to measure/calculate parameters chosen by the applicant at the end of extensive research studies, in order to quantify modifications of the intestinal mucosa possibly induced by a chronic inflammatory bowel disease in an individual.

The imaging technique used is advantageously or preferably confocal endomicroscopy. However, the processes of some embodiments can be transposed to equivalent medical imaging techniques, such as endocytoscopy (Neumann et al., Aliment Pharmacol Ther. 2011 June; 33(11):1183-93 ([7])) or high-magnification endoscopy (Kanesaka et al., Dig Endosc. 2014 January; 26(1):57-62 ([8])).

For the purposes of some embodiments, the expression "fluorescence leakage of the mucosa" is intended to mean the increase in the amount of fluorescence of the intestinal mucosa, relative to a level of fluorescence at a time t and measured within ten minutes following an intravenous injection of a fluorescent molecule into an individual. The fluorescent molecule can be any molecule known to those of ordinary skill in the art, for example fluorescein. Any method for measuring the amount of fluorescence of the intestinal mucosa that is known to those of ordinary skill in the art can be used. For example, the amount of fluorescence can be measured image by image (12 images/second) from the endomicroscopy sequences recorded. The fluorescence leakage is, in this case, the result of the slope obtained by the linear regression of the amount of fluorescence over time. The increase may be an increase of at least 5%, or at least 10%, or at least 20%, or at least 50%, or at least 60%, or at least 80%, or at least 90%, or 100%, of the fluorescence relative to the level of fluorescence at the time t. Advantageously, this parameter is a dynamic parameter, the value of which can change over time.

In the context of some embodiments, the measurement of the parameters b) to h) is carried out after definition of the contour of the opening of the crypt by the method using an active contour according to the segmentation method using exponential splines (Delgado-Gonzalo et al. "Snakes on a Plane: A Perfect Snap for Bioimage Analysis," IEEE Signal Processing Magazine, vol. 32, no. 1, pp. 41-48 ([9])).

For the purposes of some embodiments, the expression "perimeter of opening of the crypt well" is intended to mean the length of the contour of the crypt opening. The length of the contour of the crypt opening can be measured by any known and suitable method, for example by the method of Delgado-Gonzalo et al. ([9]).

The expression "Sphericity of the crypt well" is intended to mean the parameter given by the formula $4 \times \pi \times \text{Area}/\text{Perimeter of opening of the crypt well}^2$ (Wadell, H., 1932, Volume, shape, and roundness of rock particles. Journal of Geology 40:443-51 ([10])).

For the purposes of some embodiments, the expression "roundness of the crypt well" is intended to mean the parameter according to the definition of the standard ISO 1101 (ISO 1101:2012(E)). It corresponds to the standardized ratio between the maximum and minimum radii of the circles inscribed in the crypt well, expressed as a percentage.

For the purposes of some embodiments, the expression "Feret diameter of the crypt well" is intended to mean the maximum distance between two points of the surface of the crypt opening (M. R. Walter. Stromatolites. Elsevier. pp. 47—. ISBN 978-0-444-41376-5 ([11])).

For the purposes of some embodiments, the term "elongation factor of the crypt well" is intended to mean a scale factor given by the ratio between the diameter of the ellipse of the large axis having a shape closest to the crypt opening ($D_{large\ axis}$) and the diameter of the ellipse of the small axis of the ellipse having a shape closest to the crypt opening ($D_{small\ axis}$). The elongation factor is given by $D_{large\ axis}/D_{small\ axis}$.

For the purposes of some embodiments, the expression "ratio of the axes of opening of the crypt well" is intended to mean the ratio between the large axis and the small axis of the rectangle containing the crypt opening.

For the purposes of some embodiments, the expression "crypt density per field" is intended to mean a ratio between the area occupied by the crypt well openings in a field of view and the total area of the field of view.

For the purposes of some embodiments, the expression "process for quantifying" is intended to mean a process which makes it possible to quantitatively evaluate modifications of the intestinal mucosa, compared with a healthy individual, that is to say an individual not suffering from a pathological inflammatory digestive condition.

For the purposes of some embodiments, the term "confocal endomicroscopic image" is intended to mean an image, a series of images, or the reconstitution of a single image from a series of images, resulting from the implementation of confocal endomicroscopy. The series of images can for example represent a dynamic visualization, in particular in real time, of the subject studied. It may for example be a video.

The confocal endomicroscopy allows the acquisition of images in a patient, without biopsies, following the injection of a fluorescent contrast agent, for example fluorescein, during an endoscopy.

Another embodiment relates to an ex vivo process for diagnosing a chronic inflammatory bowel disease in an individual, the process including:
1) measuring, on a confocal endomicroscopic image of the digestive mucosa of an individual, the following parameters:
   a) Fluorescence leakage of the mucosa (FL),
   b) Perimeter of opening of the crypt well (PO),
   c) Sphericity of the crypt well (Spher),
   d) Roundness of the crypt well (Round),
   e) Feret diameter of the crypt well (Feret),
   f) Crypt well elongation factor (EF),
   g) Ratio of the axes of opening of the crypt well (Ma/ma),
   h) Crypt density per field (Dens);

2) selecting the values described as "higher extremes", above the thresholds defined below for each parameter:
   PO>474.62±103.10 µm,
   Spher>98.96±0.56%,
   Round>68.43±14.41%,
   Feret>169.88±51.08 µm,
   EF>1.745±0.266,
   Ma/ma>1.653±0.247,
   Dens>0.2837±0.0505;
3) comparing, for each parameter, the mean of the "higher extreme" values and the mean value of FL to a pathological threshold, the pathological threshold being defined, for each parameter, in the following way:
   FL>10.0±3.6 LUT.sec$^{-1}$,
   PO>666.40±103.10 µm,
   Spher>99.32±0.56%,
   Round>73.00±14.41%,
   Feret>186.11±51.08 µm,
   EF>1.87±0.266,
   Ma/ma>1.90±0.247,
   Dens>0.39±0.0505; and
4) assigning the following scores:
   if the mean of the "higher extreme" values of the PO, Spher, Round, Feret, EF, Ma/ma or Dens parameter, or the mean value of FL, is less than the threshold, the score of 0 is assigned to the corresponding parameter,
   if the mean of the "higher extreme" values of the PO, Spher, Round, Feret, EF, Ma/ma or Dens parameter, or the mean value of FL, is greater than the threshold, the score of 1 is assigned for FL, PO, Round, Feret and Dens and the score of 2 is assigned for Spher, EF and Ma/ma,
5) multiplying the sum of the scores by the sum of the number of values of each parameter,
   in which a total greater than 204±110 defines the individual as suffering from a chronic inflammatory bowel disease.

The parameters a) to h) measured in step 1) have been specifically selected by the applicant, after a rigorous research process, as imaging biomarkers of interest, from numerous other architectural and dynamic parameters capable of undergoing modifications in IBDs. The combination of these biomarkers also results from a rigorous and innovative selection. This group of selected biomarkers thus constitutes a group of parameters on the basis of which the diagnostic processes of some embodiments are carried out.

The applicant has also succeeded in defining a threshold, for each of these parameters, which makes it possible to select, for each parameter, the values of interest to be taken into consideration in the process for diagnosing IBDs.

Thus, at the end of step 1) of measuring the parameters a) to h), step 2) allows the selection of the values of interest, described as "higher extreme" values, for each of the parameters. In step 2), the thresholds represent, for each parameter PO, Spher, Round, Feret, EF, Ma/ma and Dens, the 90$^{th}$ centile, i.e. the lowest value of the highest 10% of values, obtained from a healthy population. The threshold is excluded from the values of interest.

The applicant has also succeeded in defining a "pathological threshold" which makes it possible to distinguish the values capable of indicating the presence of an IBD.

For the purposes of some embodiments, the term "pathological threshold" is intended to mean a value for and/or above which the parameter is considered as possibly indicating an IBD. In step 3), the pathological threshold represents, for each parameter PO, Spher, Round, Feret, EF, Ma/ma and Dens, the value which makes it possible to include at least 60% of the IBD population studied and to exclude at least 80% of the healthy population studied, these values being calculated for example on samples including about ten healthy patients and about twenty patients suffering from IBD, in particular as illustrated in example 1 hereinafter.

In the context of some embodiments, the applicant teaches the comparison of this pathological threshold with, on the one hand, the mean of the "higher extreme" values of each of the parameters b) to h) and, on the other hand, the mean value of FL.

For the purposes of some embodiments, the expression "sum of the number of values of each parameter" is intended to mean the sum of all the occurrences of each parameter that are presented on the image.

According to some embodiments, the multiplication of the sum of the scores by the sum of the number of values of each parameter makes it possible to obtain a "total", or score, or value of prediction of an IBD.

A total greater than 204±110 defines the individual as suffering from an IBD. Conversely, a score less than 204 makes it possible to classify the individual as not suffering from a chronic inflammatory bowel disease. The number 204±110 is in particular defined by the maximum score observed in the healthy population including about ten healthy patients, in particular as illustrated in example 1 hereinafter.

Another embodiment relates to an ex vivo process for the differential diagnosis of Crohn's disease versus ulcerative colitis in an individual, the process including the steps previously defined for the diagnosis of an IBD, followed, in the individual defined as suffering from an IBD, of a comparison of the mean value of FL and of the mean of the "higher extreme" values of the PO and Feret parameters, to a differential threshold defined in the following way:
  FL>19.86±5.70 LUT.sec$^{-1}$,
  PO>618.32±98.95 µm and
  Feret>204.68±29.65 µm,
in which the individual is defined as suffering from ulcerative colitis if, for each of the parameters FL, PO and Feret, a value greater than the corresponding differential threshold is reached, or the individual is defined as suffering from Crohn's disease in the opposite case.

At the end of extensive research studies, the applicant has succeeded in defining a "differential threshold" for each of the parameters FL, PO and Feret, this threshold allowing a diagnosis, in the individuals defined as suffering from IBD, either of CD, or of UC. These three parameters FL, PO and Feret were in fact selected at this stage by the applicant since it had, surprisingly, observed a significant difference between the individuals suffering from CD and those suffering from UC.

The "differential threshold" is defined, for each parameter FL, PO and Feret, as being the value which makes it possible for at least one of the IBD populations, in other words at least one population chosen from the CD population and the UC population, to be 100% represented and for the second, that is to say the one which is not 100% represented, where appropriate, to be at least 80% represented.

Regardless of the process of some embodiments used, the total number of crypts analyzed in the endomicroscopic images of the colonic mucosa can be at least 32±10 crypts for a confidence level α of 0.05 and at least 53±10 crypts for a confidence level α of 0.01. It may for example be at least approximately 20 crypts, or 40 crypts, or approximately 80 crypts, or approximately 90 crypts, or approximately 100 crypts, or approximately 120 crypts, analyzed on randomly chosen distinct colonic areas.

Regardless of the process of some embodiments used, the steps of measuring, of selecting the values, of comparing and of assigning the scores can be automated by a computer program for an a posteriori analysis of the endomicroscopy images, for example with IC-viewer (IronCAD), or by a solution integrated into the existing endomicroscopy software for real-time analysis, for example with Cellvizio (Mauna Kea Technologies).

Another embodiment relates to a computer program product which can be downloaded from a communication network and/or recorded on a medium which can be read by computer and/or which can be executed by a processor, including program code instructions for carrying out one of the processes of some embodiments.

Another embodiment relates to a system, including an endomicroscope, a visualizing device (or visualizer), and a calculator, for carrying out a process defined above.

Another embodiment relates to a system including a confocal endomicroscope connected to a visualizing device (or visualizer) and a computer including an image analyzer for measuring, on a confocal endomicroscopic image of the digestive mucosa of an individual, at least one of the parameters of the crypt well profiles (PPC) chosen from FL, PO, Spher, Round, Feret, EF, Ma/ma and Dens, and a comparator suitable for comparing the measurements carried out with the corresponding values of a healthy individual.

The analyzer of this system can be suitable for selecting values described as "higher extreme", greater than the thresholds defined below for each parameter:
  PO>474.62±103.10 µm,
  Spher>98.96±0.56%,
  Round>68.43±14.41%,
  Feret>169.88±51.08 µm,
  EF>1.745±0.266,
  Ma/ma>1.653±0.247,
  Dens>0.2837±0.0505;
and the comparator is suitable for comparing, for each parameter, the mean of the "higher extreme" values and the mean value of FL to a pathological threshold defined, for each parameter, in the following way:
  FL>10.0±3.6 LUT.sec$^{-1}$,
  PO>666.40±103.10 µm,
  Spher>99.32±0.56%,
  Round>73.00±14.41%,
  Feret>186.11±51.08 µm,
  EF>1.87±0.266,
  Ma/ma>1.90±0.247,
  Dens>0.39±0.0505;
the computer also including a score generator connected to the comparator and suitable for assigning following scores:
  if the mean of the "higher extreme" values of the PO, Spher, Round, Feret, EF, Ma/ma or Dens parameter, or the mean value of FL, is less than the threshold, the score of 0 is assigned to the corresponding parameter,
  if the mean of the "higher extreme" values of the PO, Spher, Round, Feret, EF, Ma/ma or Dens parameter, or the mean value of FL, is greater than the threshold, the score of 1 is assigned for FL, PO, Round, Feret and Dens and the score of 2 is assigned for Spher, EF and Ma/ma, and the computer also including a multiplier suitable for multiplying the sum of the scores by the sum of the number of values of each parameter.

The comparator of the system can also be suitable for comparing the mean value of FL and the mean of the "higher extreme" values of the PO and Feret parameters to a differential threshold defined in the following way:

FL>19.86±5.70 LUT.sec$^{-1}$,
PO>618.32±98.95 µm and
Feret>204.68±29.65 µm.

In other words, the system can include a confocal endomicroscope, a visualizing device (or visualizer) and a calculator, in which the calculator includes:

A) when the system relates to the implementation of the ex vivo process for quantifying the modifications of the intestinal mucosa induced by a chronic inflammatory bowel disease in an individual, devices for measuring at least one parameter chosen from FL, PO, Spher, Round, Feret, EF, Ma/ma and Dens, B) when the system relates to the implementation of the ex vivo process for diagnosing a chronic inflammatory bowel disease in an individual:
   B1) a device for measuring the FL, PO, Spher, Round, Feret, EF, Ma/ma and Dens parameters,
   B2) a selector for selecting the values described as "higher extreme", greater than the thresholds defined in this process,
   B3) a comparing device as defined in this process,
   B4) a device for assigning scores as defined in this process, and
   B5) a multiplier for multiplying scores as defined in this process;

C) when the system relates to the implementation of the ex vivo process for the differential diagnosis of Crohn's disease versus ulcerative colitis in an individual:
   C1) the devices B1) to B5), and
   C2) a comparing device as defined in this process.

Other advantages may further emerge to those of ordinary skill in the art on reading the examples below, illustrated by the appended figures, given by way of illustration.

BRIEF DESCRIPTION OF THE FIGURES

FIG. 1 represents the scheme of the principle of laser confocal endomicroscopy. The vertical rectangle at the top represents the source of laser light and the detector of the confocal system. The horizontal rectangle represents the pinhole through which light rays pass. The horizontal oval represents a focusing lens. The laser radiation passes through the center of the lens and reaches the tissue. The fluorescent molecule present in the tissue then emits light upwards. The light rays outside the focal plane are diverged by the lens and do not pass through the pinhole. The light rays emitted by the focal plane are converged by the lens toward the pinhole and the detector.

FIG. 2A represents the perimeter of opening of the crypt. FIG. 2B represents the elongation factor. FIG. 2C represents the sphericity. FIG. 2D represents the Ma/ma ratio of the crypt opening. FIG. 2E represents the roundness. FIG. 2F represents the Feret diameter. FIG. 2G represents the crypt density per field.

EXAMPLES

Example 1: Validation of Diagnostic Imaging Biomarkers for Chronic Inflammatory Bowel Diseases by Confocal Endomicroscopy Materials and Methods 5 healthy patients, 10 patients suffering from Crohn's disease (CD) in clinical inflammatory remission phase (CDAI<150) and 11 patients suffering from ulcerative colitis (UC) in clinical inflammatory remission phase (Mayo score <1) were included in this retrospective study.

The fluorescence leakage (FL) in the colonic mucosa, the perimeter of opening (PO), the roundness (Round), the sphericity (Spher), the elongation factor (EF), the Feret diameter (Feret), the large axis to small axis ratio (Ma/ma) and the crypt well density (Dens) were quantified by measuring or calculating these parameters by the confocal endomicroscopy images (ColoFlex UHD, Cellvizio, Mauna Kea Technologies).

Only the values higher than the 90$^{th}$ centile of the healthy patients were considered for the analysis (values described as "higher extremes").

Results

The quantitative analysis was carried out on 91±8 crypts per patient. It was possible to demonstrate that the mean of the values higher than the 90$^{th}$ centile of the healthy patients for the sphericity (Spher) ($p<0.01$), roundness (Round) ($p<0.05$), Feret diameter (Feret) ($p<0.05$), elongation factor (EF) ($p<0.01$), and Ma/ma ratio ($p<0.01$) are significantly higher for the CD group compared with the healthy patients (cf. FIG. 3).

The mean of the values higher than the 90$^{th}$ centile of the healthy patients for the perimeter of opening (PO) ($p<0.05$), sphericity (Spher) ($p<0.01$), Feret diameter (Feret) ($p<0.01$), elongation factor (EF) ($p<0.01$), Ma/ma ratio ($p<0.01$) and crypt image density (Dens) ($p<0.05$) are significantly higher for the UC group compared with the healthy patients (cf. FIG. 3).

The mean of the values higher than the 90$^{th}$ centile of the healthy patients for the perimeter of opening (PO) ($p<0.05$) and Feret diameter (Feret) ($p<0.05$) are significantly higher for the UC group compared with the CD group (cf. FIG. 3).

Figure 1:
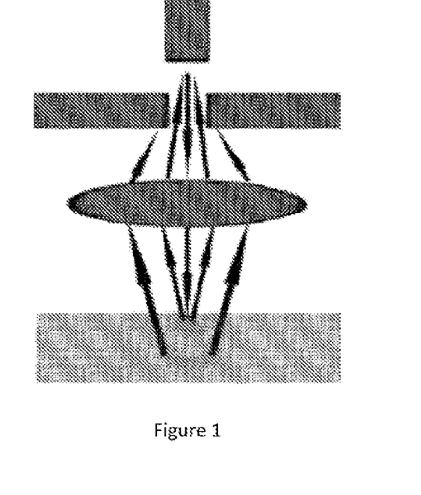
Figure 2:
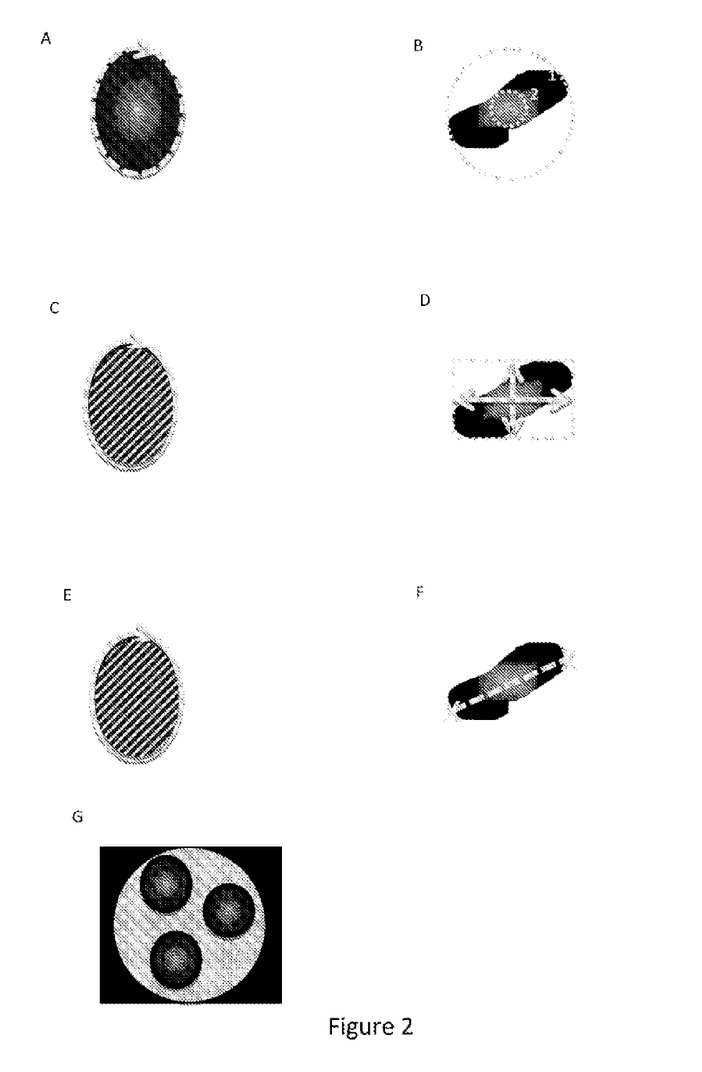
FIG. 2 represents the considered architectural parameters of the crypts.
Figure 3A:
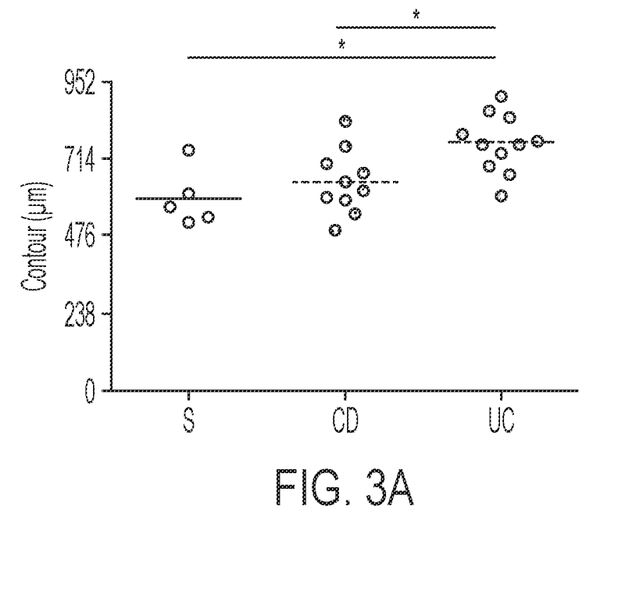
FIG. 3 represents the comparison of the mean of the values greater than the 90$^{th}$ percentile of the healthy group, for the following parameters: A: perimeter of opening of the crypt (expressed in µm), B: Sphericity (expressed as %), C: Roundness (expressed as %), D: Feret diameter (expressed in µm), E: Elongation factor, F: Ma/ma and G: Density. Each of these parameters is evaluated in 5 healthy individuals ("S"), 10 individuals suffering from Crohn's disease ("CD") and 11 individuals suffering from ulcerative colitis ("UC").
Figure 3B:
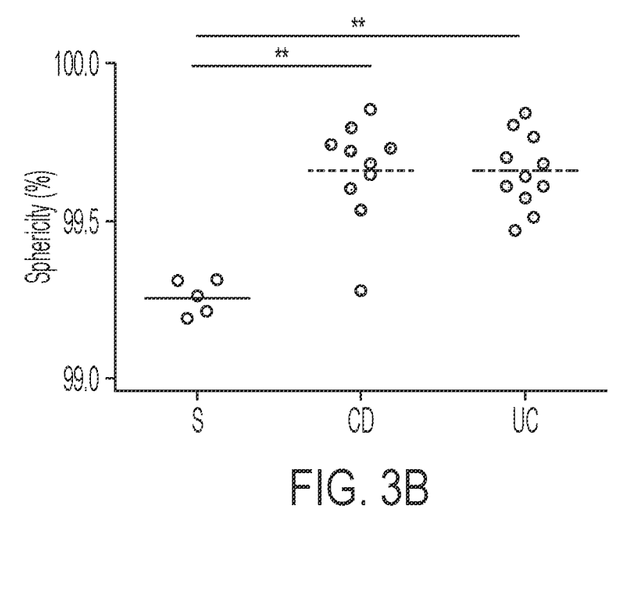
Figure 3C:
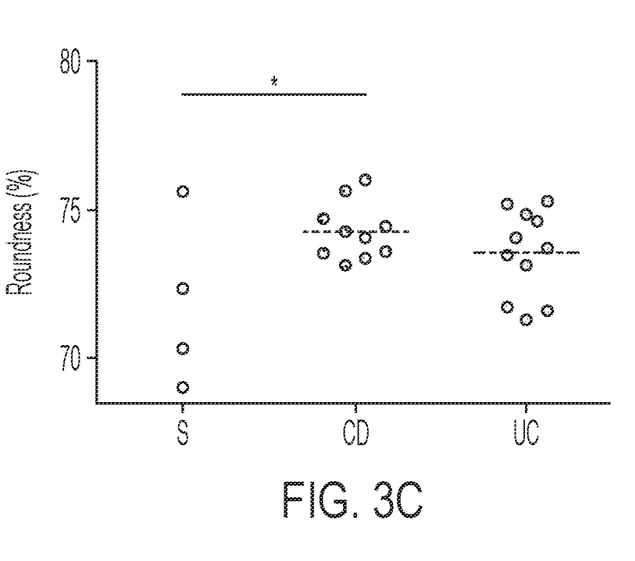
Figure 3D:
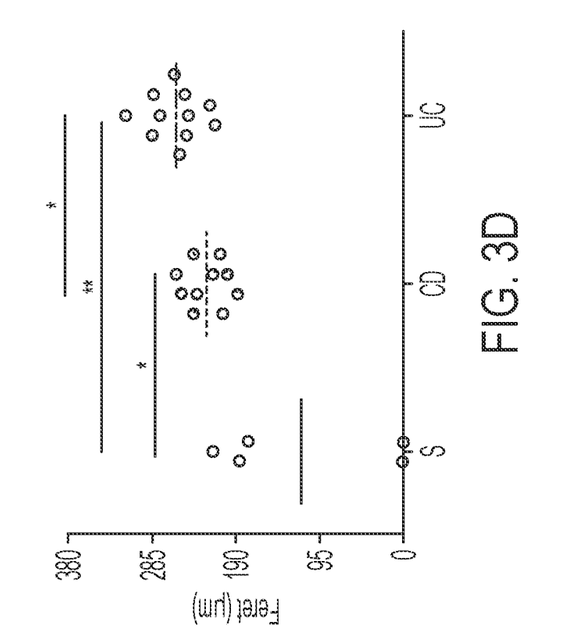
Figure 3E:
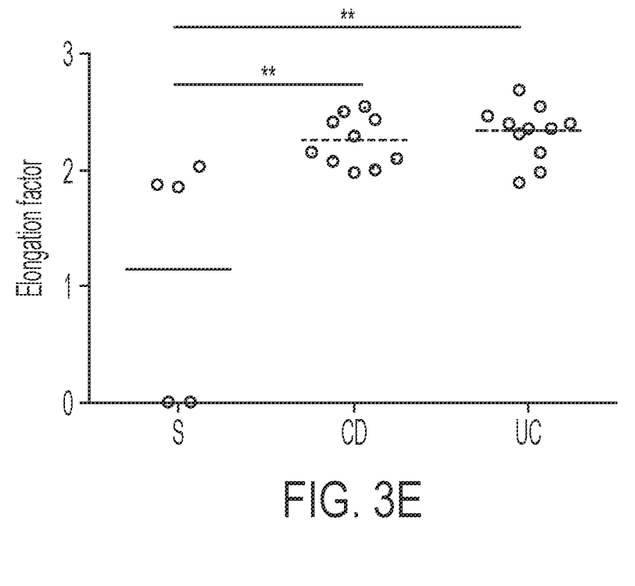
Figure 3F:
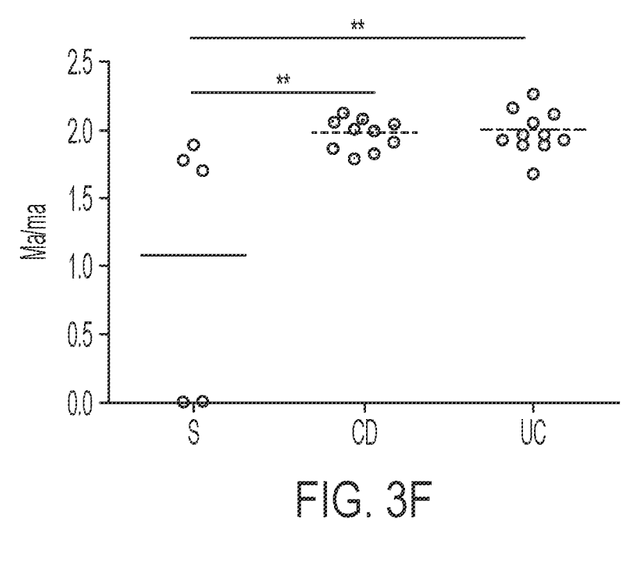
Figure 3G:
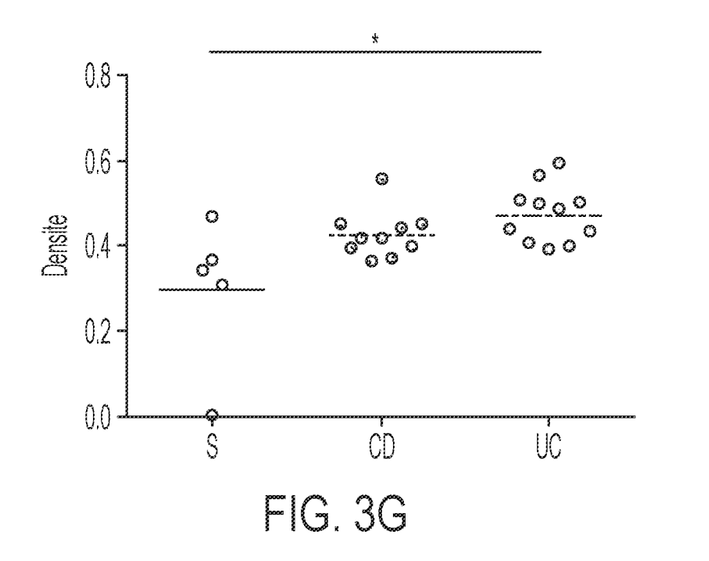
Figure 4:
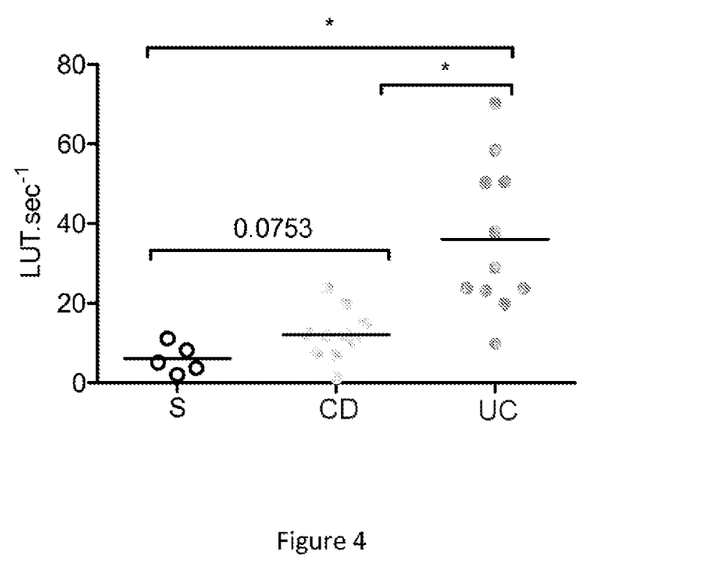
FIG. 4 represents the comparison of the mean of the fluorescence leakage (FL) values, expressed in LUT.sec$^{-1}$, in 5 healthy individuals ("S"), 10 individuals suffering from Crohn's disease ("CD") and 11 individuals suffering from ulcerative colitis ("UC").

Finally, 5.9 times more fluorescein leakage (FL) in the colonic mucosa was observed in the UC group compared with the healthy group ($p<0.05$) and 2.9 times more was observed compared with the CD group ($p<0.05$) (cf. FIG. 4).

Conclusion

This study demonstrates that it is possible to quantify the architectural modifications of the mucosa induced by IBDs, even during a clinical remission. It was possible to define 3 types of parameter: 1/ the parameters common to IBDs (sphericity, Feret diameter, elongation factor, Ma/ma); 2/ a parameter specific for Crohn's disease (Roundness) and 3/ parameters specific for ulcerative colitis (fluorescence leakage, perimeter of opening and density).

These results set down the bases for establishing an optical score for IBDs which it will be possible to use for diagnosis and monitoring of the therapeutic response.

These results also validate the use of diagnostic imaging biomarkers for IBDs and specifically for CD and UC.

Example 2: Validation of a Diagnostic Score by Endomicroscopic Imaging of IBDs, of CD and of UC Materials and Methods 5 healthy patients, 10 patients suffering from Crohn's disease (CD) in clinical inflammatory remission phase (CDAI<150) and 11 patients suffering form ulcerative colitis (UC) in clinical inflammatory remission phase (Mayo score <1) were included in this retrospective study. The fluorescence leakage (FL) in the colonic mucosa, the perimeter of opening (PO), the roundness (Round), the sphericity (Spher), the elongation factor (EF), the Feret diameter (Feret), the large axis to small axis ratio (Ma/ma) and the crypt well density (Dens) were quantified by measuring or calculating these parameters by the confocal endomicroscopy images (ColoFlex UHD, Cellvizio, Mauna Kea Technologies).

Only the values higher than the 90th centile of the healthy patients were considered for the analysis (values described as "higher extremes").

The diagnostic score for IBDs is defined by:

1—Selection of the "higher extreme" values, that is to say the values higher than the $90^{th}$ centile with the healthy patients for each of the parameters PO, Spher, Round, Feret, EF, Ma/ma and Dens.

The value of the $90^{th}$ centile of the healthy patients for each of the parameters is measured/calculated, with the following results:

PO>474.62±103.10 µm,
Spher>98.96±0.56%,
Round>68.43±14.41%,
Feret>169.88±51.08 µm,
EF>1.745±0.266,
Ma/ma>1.653±0.247,
Dens>0.2837±0.0505;

2—For each of these parameters, the mean of the "higher extreme" values, that is to say higher than the $90^{th}$ centile of the healthy patients, and the mean value of FL are compared to a pathological threshold defined by a consensus of experts. The pathological threshold, for each parameter, is thus defined by the following values:

FL>10 LUT.sec$^{-1}$,
PO>666.40 µm,
Spher>99.32%,
Round>73.00%,
Feret>186.11 µm,
EF>1.87,
Ma/ma>1.90,
Dens>0.39.

If the mean of the "higher extreme" values of the PO, Spher, Round, Feret, EF, Ma/ma or Dens parameter, or the mean value of FL, is less than the pathological threshold, the score of 0 is assigned to the parameter. If this value is greater than the pathological threshold, the score of 1 is assigned for FL, PO, Round, Feret and Dens and the score of 2 is assigned for Spher, EF and Ma/ma.

3—The sum of the scores is multiplied by the sum of the number of values of each parameter. In this example, a total greater than 204 defines the patient as suffering from an IBD.

4—For the patients defined IBD, the mean value of FL and the mean of the "higher extreme" values of PO and Feret are compared to a differential threshold defined by a consensus of experts. The differential threshold, for each of these parameters, is thus defined by the following values:

FL>19.86 LUT.sec$^{-1}$,
PO>618.32 µm
Feret>618.32 µm.

If, for each of these 3 parameters, a value greater than the differential threshold corresponding to the parameter in question is measured/calculated, then the patient is defined as suffering from UC. In the opposite case, that is to say if at least one of the parameters does not have a value greater than the differential threshold of the corresponding parameter, then the patient is defined as suffering from CD.

Results

The values of the $90^{th}$ centile of the healthy population are: Perimeter of opening (>474.62 µm), Sphericity (>98.96%), Roundness (>68.43%), Feret diameter (>169.88 µm), Elongation factor (>1.745), Ma/ma (>1.653) and Density (>0.2837).

The values, occurrences, scores and diagnoses of IBD are summarized in table 1. The specificity, the sensitivity, the positive predictive value (PPV) and the negative predictive value (NPV) are 100% for this group of patients.

TABLE 1

| | | | Perimeter of opening | | | Sphericity | | | Roundness | | | Feret diameter | | |
|---|---|---|---|---|---|---|---|---|---|---|---|---|---|---|
| Patient | | | Mean | Point | Occurrence | Mean | Point | Occurrence | Mean | Point | Occurrence | Mean | Point | Occurrence |
| 1 | healthy | | 564.06 | 0 | 7 | 99.31 | 0 | 5 | 70.35 | 0 | 9 | 0 | 0 | 0 |
| 2 | healthy | | 603.092 | 0 | 4 | 99.26 | 0 | 3 | 72.33 | 0 | 4 | 0 | 0 | 0 |
| 3 | healthy | | 737.324 | 1 | 4 | 99.19 | 0 | 2 | 75.6 | 1 | 2 | 216.3896 | 1 | 8 |
| 4 | healthy | | 515.508 | 0 | 3 | 99.21 | 0 | 2 | 0 | 0 | 0 | 175.9772 | 0 | 9 |
| 5 | healthy | | 525.98 | 0 | 1 | 99.31 | 0 | 7 | 69.02 | 0 | 4 | 185.9256 | 0 | 2 |
| 6 | IBD | CD | 584.052 | 0 | 6 | 99.6 | 2 | 21 | 73.36 | 1 | 24 | 201.11 | 1 | 7 |
| 7 | IBD | CD | 612.612 | 0 | 9 | 99.53 | 2 | 7 | 73.12 | 1 | 10 | 216.342 | 1 | 6 |
| 8 | IBD | CD | 642.124 | 0 | 44 | 99.74 | 2 | 16 | 74.67 | 1 | 24 | 237.3336 | 1 | 56 |
| 9 | IBD | CD | 544.544 | 0 | 17 | 99.27 | 0 | 3 | 75.62 | 1 | 10 | 206.4888 | 1 | 28 |
| 10 | IBD | CD | 667.828 | 1 | 31 | 99.68 | 2 | 32 | 73.64 | 1 | 37 | 235.1916 | 1 | 47 |
| 11 | IBD | CD | 825.384 | 1 | 6 | 99.85 | 2 | 27 | 76 | 1 | 29 | 256.1356 | 1 | 10 |
| 12 | IBD | CD | 751.128 | 1 | 31 | 99.72 | 2 | 6 | 74.2 | 1 | 7 | 249.8524 | 1 | 41 |
| 13 | IBD | CD | 695.436 | 1 | 19 | 99.65 | 2 | 24 | 74 | 1 | 19 | 238.714 | 1 | 34 |
| 14 | IBD | CD | 490.756 | 0 | 1 | 99.73 | 2 | 13 | 73.54 | 1 | 24 | 186.6396 | 1 | 6 |
| 15 | IBD | CD | 593.096 | 0 | 8 | 99.79 | 2 | 13 | 74.43 | 1 | 20 | 202.9188 | 1 | 20 |
| 16 | IBD | CD | 754.936 | 1 | 21 | 99.57 | 2 | 7 | 75.29 | 1 | 8 | 247.996 | 1 | 30 |
| 17 | IBD | UC | 857.752 | 1 | 11 | 99.8 | 2 | 54 | 74.61 | 1 | 57 | 252.518 | 1 | 18 |
| 18 | IBD | UC | 766.836 | 1 | 35 | 99.7 | 2 | 20 | 73.14 | 1 | 19 | 260.6576 | 1 | 43 |

TABLE 1-continued

| | | | | | | | | | | | | | | |
|---|---|---|---|---|---|---|---|---|---|---|---|---|---|---|
| 19 | IBD | UC | 689.248 | 1 | 10 | 99.64 | 2 | 17 | 74.05 | 1 | 30 | 219.3408 | 1 | 15 |
| 20 | IBD | UC | 904.4 | 1 | 16 | 99.61 | 2 | 36 | 75.22 | 1 | 40 | 313.3984 | 1 | 16 |
| 21 | IBD | UC | 731.136 | 1 | 3 | 99.76 | 2 | 40 | 73.45 | 1 | 39 | 276.7464 | 1 | 4 |
| 22 | IBD | UC | 601.664 | 0 | 5 | 99.51 | 2 | 9 | 71.72 | 0 | 29 | 212.8672 | 1 | 8 |
| 23 | IBD | UC | 666.4 | 0 | 13 | 99.61 | 2 | 39 | 73.67 | 1 | 60 | 246.7584 | 1 | 15 |
| 24 | IBD | UC | 838.236 | 1 | 3 | 99.47 | 2 | 12 | 74.86 | 1 | 20 | 243.5692 | 1 | 6 |
| 25 | IBD | UC | 753.508 | 1 | 35 | 99.84 | 2 | 6 | 71.34 | 0 | 10 | 282.744 | 1 | 37 |
| 26 | IBD | UC | 788.256 | 1 | 31 | 99.68 | 2 | 9 | 71.64 | 0 | 9 | 285.4572 | 1 | 34 |

| Elongation factor | | | Ma/ma | | | Density | | | Fluorescence leakage | | | IBD diagnostic score (retrospective) | |
|---|---|---|---|---|---|---|---|---|---|---|---|---|---|
| Mean | Point | Occurrence | Mean | Point | Occurrence | Mean | Point | Occurrence | Mean | Point | Occurrence | | |
| 0 | 0 | 0 | 0 | 0 | 0 | 0.3672 | 0 | 3 | 11.15 | 1 | NA | 24 | healthy |
| 1.869 | 0 | 10 | 1.784 | 0 | 10 | 0.3426 | 0 | 4 | 5.1 | 0 | NA | 0 | healthy |
| 2.021 | 2 | 6 | 1.884 | 0 | 7 | 0.4695 | 1 | 5 | 2.08 | 0 | NA | 204 | healthy |
| 1.843 | 0 | 3 | 1.712 | 0 | 2 | 0 | 0 | 0 | 3.77 | 0 | NA | 0 | healthy |
| 0 | 0 | 0 | 0 | 0 | 0 | 0.3114 | 0 | 1 | 8.26 | 0 | NA | 0 | healthy |
| 2.092 | 2 | 16 | 2.121 | 2 | 9 | 0.4217 | 1 | 15 | 12.14 | 1 | NA | 980 | IBD |
| 1.968 | 2 | 3 | 1.787 | 0 | 3 | 0.3645 | 0 | 7 | 19.87 | 1 | NA | 315 | IBD |
| 2.426 | 2 | 43 | 2.015 | 2 | 22 | 0.4429 | 1 | 47 | 10.21 | 1 | NA | 2520 | IBD |
| 2.074 | 2 | 24 | 1.865 | 0 | 8 | 0.5579 | 1 | 29 | 12.4 | 1 | NA | 714 | IBD |
| 2.536 | 2 | 42 | 2.074 | 2 | 28 | 0.4522 | 1 | 48 | 6.835 | 0 | NA | 2650 | IBD |
| 2.146 | 2 | 8 | 1.814 | 0 | 4 | 0.4202 | 1 | 43 | 11.97 | 1 | NA | 1143 | IBD |
| 2.493 | 2 | 22 | 2.061 | 2 | 10 | 0.3713 | 0 | 15 | 14.92 | 1 | NA | 1320 | IBD |
| 2.4 | 2 | 38 | 1.993 | 2 | 25 | 0.4494 | 1 | 40 | 1.32 | 0 | NA | 1990 | IBD |
| 1.995 | 2 | 17 | 1.915 | 2 | 9 | 0.3983 | 1 | 17 | 7.64 | 0 | NA | 783 | IBD |
| 2.284 | 2 | 28 | 2.045 | 2 | 11 | 0.3956 | 1 | 22 | 23.68 | 1 | NA | 1220 | IBD |
| 2.313 | 2 | 20 | 2.109 | 2 | 15 | 0.4855 | 1 | 32 | 19.87 | 1 | NA | 1463 | IBD |
| 1.976 | 2 | 24 | 1.898 | 0 | 18 | 0.4375 | 1 | 37 | 28.87 | 1 | NA | 1971 | IBD |
| 2.347 | 2 | 34 | 2.164 | 2 | 20 | 0.5083 | 1 | 44 | 9.81 | 0 | NA | 2150 | IBD |
| 2.389 | 2 | 24 | 1.973 | 2 | 18 | 0.4977 | 1 | 37 | 23.82 | 1 | NA | 1661 | IBD |
| 2.39 | 2 | 12 | 1.967 | 2 | 5 | 0.5951 | 1 | 17 | 70.32 | 1 | NA | 1562 | IBD |
| 2.539 | 2 | 4 | 1.914 | 2 | 2 | 0.3929 | 1 | 16 | 37.88 | 1 | NA | 1188 | IBD |
| 2.358 | 2 | 8 | 1.927 | 2 | 6 | 0.4042 | 1 | 17 | 50.59 | 1 | NA | 738 | IBD |
| 2.147 | 2 | 19 | 1.921 | 2 | 9 | 0.4305 | 1 | 26 | 23.79 | 1 | NA | 1810 | IBD |
| 1.893 | 2 | 4 | 1.675 | 0 | 2 | 0.4 | 1 | 23 | 50.41 | 1 | NA | 630 | IBD |
| 2.681 | 2 | 28 | 2.271 | 2 | 17 | 0.5042 | 1 | 45 | 58.6 | 1 | NA | 1780 | IBD |
| 2.461 | 2 | 29 | 2.065 | 2 | 16 | 0.5632 | 1 | 37 | 23.15 | 1 | NA | 1650 | IBD |

The values and differential diagnoses are summarized in table 2.

For the CD diagnosis, the specificity is 87.5%, the sensitivity is 100%, the PPV is 83.3% and the NPV is 100%.

For the UC diagnosis, the specificity is 100%, the sensitivity is 81.8%, the PPV is 100% and the NPV is 88.2%.

Conclusion

This study demonstrates that the endomicroscopic score established enables the diagnosis of an IBD, even in a state of clinical inflammatory remission. This score coupled to the use of 3 other biomarkers (FL, PO and Feret diameter) also makes it possible to distinguish between CD and UC.

TABLE 2

| Patient | | | IBD diagnostic score (retrospective) | | Perimeter of opening | Feret diameter | Fluorescence leakage | Differential diagnosis |
|---|---|---|---|---|---|---|---|---|
| 6 | IBD | CD | 980 | IBD | 584.052 | 201.11 | 12.14 | CD |
| 7 | IBD | CD | 315 | IBD | 612.612 | 216.342 | 19.87 | CD |
| 8 | IBD | CD | 2520 | IBD | 642.124 | 237.3336 | 10.21 | CD |
| 9 | IBD | CD | 714 | IBD | 544.544 | 206.4888 | 12.4 | CD |
| 10 | IBD | CD | 2650 | IBD | 667.828 | 235.1916 | 6.835 | CD |
| 11 | IBD | CD | 1143 | IBD | 825.384 | 256.1356 | 11.97 | CD |
| 12 | IBD | CD | 1320 | IBD | 751.128 | 249.8524 | 14.92 | CD |
| 13 | IBD | CD | 1990 | IBD | 695.436 | 238.714 | 1.32 | CD |
| 14 | IBD | CD | 783 | IBD | 490.756 | 186.6396 | 7.64 | CD |
| 15 | IBD | CD | 1220 | IBD | 593.096 | 202.9188 | 23.68 | CD |
| 16 | IBD | CD | 1463 | IBD | 754.936 | 247.996 | 19.87 | UC |
| 17 | IBD | UC | 1971 | IBD | 857.752 | 252.518 | 28.87 | UC |
| 18 | IBD | UC | 2150 | IBD | 766.836 | 260.6576 | 9.81 | CD |
| 19 | IBD | UC | 1661 | IBD | 689.248 | 219.3408 | 23.82 | UC |
| 20 | IBD | UC | 1562 | IBD | 904.4 | 313.3984 | 70.32 | UC |
| 21 | IBD | UC | 1188 | IBD | 731.136 | 276.7464 | 37.88 | UC |
| 22 | IBD | UC | 738 | IBD | 601.664 | 212.8672 | 50.59 | CD |
| 23 | IBD | UC | 1810 | IBD | 666.4 | 246.7584 | 23.79 | UC |
| 24 | IBD | UC | 630 | IBD | 838.236 | 243.5692 | 50.41 | UC |
| 25 | IBD | UC | 1780 | IBD | 753.508 | 282.744 | 58.6 | UC |
| 26 | IBD | UC | 1650 | IBD | 788.256 | 285.4572 | 23.15 | UC |

Example 3: Validation of a Diagnostic Score by Endomicroscopic Imaging for IBDs (CD and UC)

Materials and Methods 4 healthy patients, 13 patients suffering from Crohn's disease (CD) in clinical inflammatory remission phase (CDAI<150) and 16 patients suffering from ulcerative colitis (UC) in clinical inflammatory remission phase (Mayo score <1) were included in this retrospective study. The parameters described in example 2 were quantified by measuring or calculating these parameters by the confocal endomicroscopy images (ColoFlex UHD, Cellvizio, Mauna Kea Technologies).

Only the values higher than the $90^{th}$ centile of the healthy patients were considered for the analysis (values described as "higher extreme"). The diagnostic score is constructed as previously described. The differential diagnosis is constructed on the basis of FL (>19.86±5.70 LUT.$sec^{-1}$), PO (>618.32±98.95 µm) and Feret (>204.68±29.65 µm) as previously described.

Results

The results are summarized in table 3.

The whole of the population studied (example 2 and example 3) demonstrates that the diagnostic score enables the identification of an IBD with a sensitivity of 98% and a specificity of 89%. The differential diagnosis has a sensitivity of 65.4% and a specificity of 75%.

LIST OF REFERENCES

1. Tontini et al., World J. Gastroenterol, 2016 Jan. 21, 2016 January 21; 22(3):1246-59.
2. Kiesslich et al., Gastroenterology 2007, 132:874-882.
3. Li et al., Am J Gastroenterol 2010; 105:1391-1396.
4. Neumann et al., Inflamm Bowel Dis. 2012 December; 18(12):2261-9.
5. Liu et al., Gastrointest. Endosc. 2011, 73:1174-1180.
6. Musquer et al., Dig Liver Dis 2013, 45:487-492.
7. Neumann et al., Aliment Pharmacol Ther. 2011 June; 33(11):1183-93.
8. Kanesaka et al., Dig Endosc. 2014 January; 26(1):57-62.
9. Delgado-Gonzalo et al. "Snakes on a Plane: A Perfect Snap for Bioimage Analysis," IEEE Signal Processing Magazine, vol. 32, no. 1, pp. 41-48.

TABLE 3

| Patient No. series 2 | Diagnosis at inclusion | Retrospective diagnosis | | Differential diagnosis | | | |
|---|---|---|---|---|---|---|---|
| | | Score | Healthy/IBD | FL | PO | Feret | CD/UC |
| 1 | Healthy | 1 | Healthy | | | | |
| 2 | Healthy | 172 | Healthy | | | | |
| 3 | Healthy | 0 | Healthy | | | | |
| 4 | Healthy | 296 | IBD | | | | |
| 5 | CD | 720 | IBD | 20.87 | 744.75 | 367.26 | UC |
| 6 | CD | 456 | IBD | 23.185 | 557.93 | 206.21 | CD |
| 7 | CD | 1211 | IBD | 9.9 | 847.17 | 296.94 | CD |
| 8 | CD | 2000 | IBD | 11.21 | 728.88 | 262.29 | CD |
| 9 | CD | 1152 | IBD | 13.95 | 859.54 | 311.17 | CD |
| 10 | CD | 627 | IBD | 6.06 | 677.67 | 238.51 | CD |
| 11 | CD | 1184 | IBD | 22.46 | 697.33 | 251.08 | UC |
| 12 | CD | 1140 | IBD | 34.18 | 708.28 | 254.43 | UC |
| 13 | CD | 2112 | IBD | 33.41 | 553.52 | 201.3 | CD |
| 14 | CD | 62 | Healthy | 3.89 | 0 | 0 | CD |
| 15 | CD | 3374 | IBD | 8.16 | 875.5 | 314.47 | CD |
| 16 | CD | 1904 | IBD | 16.56 | 889.23 | 328.48 | UC |
| 17 | CD | 1112 | IBD | 19.49 | 859.54 | 311.17 | UC |
| 18 | UC | 252 | IBD | 7.326 | 647.17 | 225.6 | CD |
| 19 | UC | 3724 | IBD | 26.14 | 697.06 | 240.68 | UC |
| 20 | UC | 1435 | IBD | 19.4675 | 741.9 | 258.98 | UC |
| 21 | UC | 3530 | IBD | 29.96 | 664.13 | 246.18 | UC |
| 22 | UC | 1425 | IBD | 7.326667 | 719.18 | 264.71 | CD |
| 23 | UC | 425 | IBD | 22.614 | 647.28 | 232.59 | UC |
| 24 | UC | 930 | IBD | 44.374 | 707.06 | 242.93 | UC |
| 25 | UC | 3059 | IBD | 37.88 | 605.3 | 215.47 | CD |
| 26 | UC | 1362 | IBD | 18.784 | 736.61 | 242.4 | UC |
| 27 | UC | 748 | IBD | 12.6 | 690.25 | 236.94 | CD |
| 28 | UC | 1350 | IBD | 23.84 | 689.14 | 238.69 | UC |
| 29 | UC | 355 | IBD | 3.416667 | 655.85 | 223.13 | CD |
| 30 | UC | 258 | IBD | 14.52 | 615.79 | 215.41 | CD |
| 31 | UC | 978 | IBD | 19.30667 | 664.56 | 231.84 | UC |
| 32 | UC | 3240 | IBD | 7.43 | 758.54 | 275.53 | CD |
| 33 | US | 1115 | IBD | 21.935 | 696.47 | 242.17 | UC |

The sensitivity of the IBD diagnosis is 96.55% for a specificity of 75%. The sensitivity of the UC/CD differential diagnosis is 68.75% for a specificity of 61.54%.

Conclusion

This study demonstrates the validity of the endomicroscopic score established and enables the diagnosis of an IBD, even in clinical inflammatory remission state. This score coupled to the use of 3 other biomarkers (FL, PO and Feret) also makes it possible to distinguish between CD and UC.

10. Wadell, H., 1932, Volume, shape, and roundness of rock particles. Journal of Geology 40:443-51.
11. M. R. Walter. Stromatolites. Elsevier. pp. 47, ISBN 978-0-444-41376-5.

The invention claimed is:

1. An ex vivo process for quantifying the modifications of the intestinal mucosa induced by a chronic inflammatory bowel disease in an individual, the process comprising:

1) Measuring, on a confocal endomicroscopic image of a digestive mucosa of an individual, following crypt well profile (PPC) parameters:
   a) Fluorescence leakage of the mucosa (FL),
   b) Perimeter of opening of the crypt well (PO),
   c) Sphericity of the crypt well (Spher),
   d) Roundness of the crypt well (Round),
   e) Feret diameter of the crypt well (Feret),
   f) Crypt well elongation factor (EF),
   g) Ratio of axes of opening of the crypt well (Ma/ma),
   h) Crypt density per field (Dens); and
2) quantifying modifications of the parameters a) to h) compared with corresponding parameters of a healthy individual.

2. An ex vivo process for diagnosing a chronic inflammatory bowel disease in an individual, the process comprising:
   1) Measuring, on a confocal endomicroscopic image of digestive mucosa of an individual, following parameters:
      a) Fluorescence leakage of the mucosa (FL),
      b) Perimeter of opening of the crypt well (PO),
      c) Sphericity of a crypt well (Spher),
      d) Roundness of the crypt well (Round),
      e) Feret diameter of the crypt well (Feret),
      f) Crypt well elongation factor (EF),
      g) Ratio of axes of opening of the crypt well (Ma/ma),
      h) Crypt density per field (Dens);
   2) Selecting values described as "higher extremes", above thresholds defined below for each parameter:
      PO>474.62±103.10 μm,
      Spher>98.96±0.56%,
      Round>68.43±14.41%,
      Feret>169.88±51.08 μm,
      EF>1.745±0.266,
      Ma/ma>1.653±0.247,
      Dens>0.2837±0.0505;
   3) Comparing, for each parameter, the mean of the "higher extreme" values and the mean value of FL to a pathological threshold, the pathological threshold being defined, for each parameter, in a following way:
      FL>10.0±3.6 LUT.sec$^{-1}$,
      PO>666.40±103.10 μm,
      Spher>99.32±0.56%,
      Round>73.00±14.41%,
      Feret>186.11±51.08 μm,
      EF>1.87±0.266,
      Ma/ma>1.90±0.247,
      Dens>0.39±0.0505;
   4) Assigning following scores:
      if the mean of the "higher extreme" values of each parameter PO, Spher, Round, Feret, EF, Ma/ma and Dens, or the mean value of FL, is less than the pathological threshold, the score of 0 is assigned to a corresponding parameter,
      if the mean of the "higher extreme" values of each parameter PO, Spher, Round, Feret, EF, Ma/ma and Dens, or the mean value of FL, is greater than the pathological threshold, a score of 1 is assigned for FL, PO, Round, Feret and Dens, and a score of 2 is assigned for Spher, EF and Ma/ma, and
   5) Multiplying the sum of the scores by the sum of the number of values of each parameter,
   in which a total greater than 204±110 defines the individual as suffering from a chronic inflammatory bowel disease.

3. An ex vivo process for a differential diagnosis of Crohn's disease versus ulcerative colitis in an individual, the process comprising:
   the process defined in claim 2,
   followed, in the individual defined as suffering from an IBD, by a comparison of the mean value of FL and of the mean of the "higher extreme" values of the PO and Feret parameters, to a differential threshold defined in the following way:
      FL>19.86±5.70 LUT.sec$^{-1}$,
      PO>618.32±98.95 μm and
      Feret>204.68±29.65 μm,
   in which the individual is defined as suffering from ulcerative colitis if, for each of the parameters FL, PO and Feret, a value greater than the corresponding differential threshold is reached, or
   the individual is defined as suffering from Crohn's disease in an opposite case.

4. The process as claimed in claim 1, wherein the total number of crypts analyzed in the endomicroscopic image of the digestive mucosa is greater than 20.

5. The process as claimed in claim 1, wherein the steps of measuring, of selecting values, of comparing and of assigning scores are automated by a computer program, stored on a non-statutory computer readable medium, for an a posteriori analysis of the endomicroscopy images or by a solution integrated into existing endomicroscopy software for a real-time analysis.

6. A computer program product, stored on a non-statutory computer readable medium, which can be downloaded from a communication network and/or recorded on a medium which can be read by computer and/or which can be executed by a processor, comprising:
   program code instructions for carrying out the process as claimed in claim 1, the computer program being executed on a computer or a processor.

7. A system, comprising:
   an endomicroscope,
   a visualizer, and
   a computer comprising image analysis means for measuring, for carrying out the process of claim 1.

8. The system as claimed in claim 7, wherein the endomicroscope is a confocal endomicroscope connected to a visualizer and a computer, the computer comprising an image analyzer for measuring, on a confocal endomicroscopic image of the digestive mucosa of an individual, parameters of the profiles of the crypt wells (PPC) chosen from FL, PO, Spher, Round, Feret, EF, Ma/ma and Dens, and a comparator suitable for comparing the measurements carried out with the corresponding values of a healthy individual.

9. The system as claimed in claim 8, wherein the image analysis means is suitable for selecting values described as "higher extreme", greater than thresholds defined below for each parameter:
   PO>474.62±103.10 μM,
   Spher>98.96±0.56%,
   Round>68.43±14.41%,
   Feret>169.88±51.08 μm,
   EF>1.745±0.266,
   Ma/ma>1.653±0.247,
   Dens>0.2837±0.0505;
   and the comparator is suitable for comparing, for each parameter, the mean of the "higher extreme" values and the mean value of FL to a pathological threshold defined, for each parameter, in a following way:

FL>10.0±3.6 LUT.sec$^{-1}$,
PO>666.40±103.10 μm,
Spher>99.32±0.56%,
Round>73.00±14.41%,
Feret>186.11±51.08 μm,
EF>1.87±0.266,
Ma/ma>1.90±0.247,
Dens>0.39±0.0505;
the computer also including a score generator connected to the comparator and suitable for assigning following scores:
if the mean of the "higher extreme" values of the PO, Spher, Round, Feret, EF, Ma/ma or Dens parameter, or the mean value of FL, is less than the threshold, a score of 0 is assigned to the corresponding parameter,
if the mean of the "higher extreme" values of the PO, Spher, Round, Feret, EF, Ma/ma or Dens parameter, or the mean value of FL, is greater than the threshold, a score of 1 is assigned for FL, PO, Round, Feret and Dens and a score of 2 is assigned for Spher, EF and Ma/ma,
and the computer also comprising a multiplier suitable for multiplying the sum of the scores by the sum of the number of values of each parameter.

10. The system as claimed in claim 9, wherein the comparator is suitable for comparing the mean value of FL and the mean of the "higher extreme" values of the PO and Feret parameters to a differential threshold defined in the following way:
FL>19.86±5.70 LUT.sec$^{-1}$,
PO>618.32±98.95 μm and
Feret>204.68±29.65 μm.

11. The process as claimed in claim 2, wherein the total number of crypts analyzed in the endomicroscopic image of the digestive mucosa is greater than 20.

12. The process as claimed in claim 3, wherein the total number of crypts analyzed in the endomicroscopic image of the digestive mucosa is greater than 20.

13. The process as claimed in claim 2, wherein the steps of measuring, of selecting the values, of comparing and of assigning the scores are automated by a computer program, stored on a non-statutory computer readable medium, for an a posteriori analysis of the endomicroscopy images or by a solution integrated into the existing endomicroscopy software for a real-time analysis.

14. The process as claimed in claim 3, wherein the steps of measuring, of selecting the values, of comparing and of assigning the scores are automated by a computer program, stored on a non-statutory computer readable medium, for an a posteriori analysis of the endomicroscopy images or by a solution integrated into the existing endomicroscopy software for a real-time analysis.

15. The process as claimed in claim 4, wherein the steps of measuring, of selecting values, of comparing and of assigning scores are automated by a computer program, stored on a non-statutory computer readable medium, for an a posteriori analysis of the endomicroscopy images or by a solution integrated into existing endomicroscopy software for a real-time analysis.

16. A computer program product, stored on a non-statutory computer readable medium, which can be downloaded from a communication network and/or recorded on a medium which can be read by computer and/or which can be executed by a processor, comprising:
program code instructions for carrying out the process as claimed in claim 2, the computer program being executed on a computer or a processor.

17. A computer program product, stored on a non-statutory computer readable medium, which can be downloaded from a communication network and/or recorded on a medium which can be read by computer and/or which can be executed by a processor, comprising:
program code instructions for carrying out the process as claimed in claim 3, the computer program being executed on a computer or a processor.

18. A system, comprising:
an endomicroscope,
a visualizer, and
a calculator, for carrying out the process of claim 2.

19. A system, comprising:
an endomicroscope,
a visualizer, and
a calculator, for carrying out the process of claim 3.

* * * * *